(12) United States Patent
Gustavsson et al.

(10) Patent No.: US 9,532,834 B2
(45) Date of Patent: *Jan. 3, 2017

(54) LASER SHAVING

(71) Applicants: Morgan Lars Ake Gustavsson, Newport Beach, CA (US); Paul Binun, Chula Vista, CA (US)

(72) Inventors: Morgan Lars Ake Gustavsson, Newport Beach, CA (US); Paul Binun, Chula Vista, CA (US)

(*) Notice: Subject to any disclaimer, the term of this patent is extended or adjusted under 35 U.S.C. 154(b) by 8 days.

This patent is subject to a terminal disclaimer.

(21) Appl. No.: 14/694,994

(22) Filed: Apr. 23, 2015

(65) Prior Publication Data

US 2015/0223889 A1  Aug. 13, 2015

Related U.S. Application Data

(63) Continuation of application No. 14/210,248, filed on Mar. 13, 2014, now Pat. No. 9,017,322.
(Continued)

(51) Int. Cl.
*A61B 18/20* (2006.01)
*A61B 18/22* (2006.01)
*A61B 18/00* (2006.01)

(52) U.S. Cl.
CPC .............. *A61B 18/203* (2013.01); *A61B 18/22* (2013.01); *A61B 2018/00476* (2013.01);
(Continued)

(58) Field of Classification Search
CPC ........... A61B 2018/00476; A61B 2018/00779; A61B 2018/202; A61B 2018/2261; A61B 18/203; A61B 18/22; A61B 2018/2244; A61B 18/225; A61B 2018/2288

See application file for complete search history.

(56) References Cited

U.S. PATENT DOCUMENTS 4,617,926 A  10/1986 Sutton
5,606,798 A  3/1997 Kelman
(Continued)

OTHER PUBLICATIONS

Jul. 4, 2014 International Search Report and Written Opinion for Application No. PCT.US2014/027674 filed Mar. 14, 2014.

*Primary Examiner* — Gary Jackson
*Assistant Examiner* — Scott T Luan
(74) *Attorney, Agent, or Firm* — Knobbe, Martens, Olson & Bear, LLP.

(57) ABSTRACT

A device configured to cut hair using laser light includes a handle portion and a shaving portion. The handle portion includes a battery and a laser light source. The laser light source is coupled to and configured to receive power from the battery. The laser light source is also configured to generate laser light having a wavelength selected to target a predetermined chromophore to effectively cut a hair shaft. The shaving portion includes a support and a single fiber optic supported by the support. The fiber optic has a proximal end, a distal end, an outer wall, and a cutting region positioned towards the distal end and extending along a portion of the side wall. The fiber optic is positioned to receive the laser light from the laser light source at the proximal end, conduct the laser light from the proximal end toward the distal end, and emit the light out of the cutting region and toward hair when the cutting region is brought in contact with the hair.

24 Claims, 5 Drawing Sheets

Related U.S. Application Data

(60) Provisional application No. 61/801,162, filed on Mar. 15, 2013.

(52) U.S. Cl.
CPC ........... *A61B 2018/00779* (2013.01); *A61B 2018/202* (2013.01); *A61B 2018/225* (2013.01); *A61B 2018/2244* (2013.01); *A61B 2018/2261* (2013.01); *A61B 2018/2288* (2013.01)

(56) References Cited

U.S. PATENT DOCUMENTS

| | | | |
|---|---|---|---|
| 5,735,844 A * | 4/1998 | Anderson | A61B 18/203 606/9 |
| 6,030,378 A | 2/2000 | Stewart | |
| 6,129,723 A | 10/2000 | Anderson et al. | |
| 2006/0293728 A1 * | 12/2006 | Roersma | A61N 5/0617 607/88 |
| 2008/0201954 A1 | 8/2008 | Meinschien | |
| 2008/0244912 A1 | 10/2008 | Gustavsson | |
| 2009/0264872 A1 | 10/2009 | Van Hal et al. | |
| 2012/0123444 A1 | 5/2012 | Verhagen et al. | |

* cited by examiner

LASER SHAVING

CROSS-REFERENCE TO RELATED APPLICATIONS

The present application is a continuation of U.S. application Ser. No. 14/210,248, filed Mar. 13, 2014, now U.S. Pat. No. 9,017,322, which claims the priority benefit of U.S. Provisional Application No. 61/801,162, filed Mar. 15, 2013, the entireties of which are hereby incorporated by reference herein.

BACKGROUND

Field

The present disclosure generally relates to devices and methods for cutting or processing matter using light, including but not limited to shaving using laser light.

Description of the Related Art

Shaving is most commonly performed using razors having one or more metal blades. However, razors can irritate and damage the user's skin. Razors are also limited to removing hair at the surface of the skin, which results in the hair becoming visible again in a relatively short time period. Various laser devices are also available for hair removal. However, laser hair removal devices and methods typically involve using laser light to destroy the hair follicle below the skin surface for permanent or semi-permanent hair removal. Such devices and methods are typically more dangerous, expensive, not suitable for home use, and often do not provide effective cutting of lighter colored hair.

SUMMARY

The present disclosure describes devices and methods for cutting matter, including but not limited to shaving hair. In some embodiments, a shaving device uses electromagnetic radiation or light (e.g., laser or other light energy) to cut or damage one or more hair shafts. At least one surface of at least one fiber or a light guide can emit light towards at least one hair shaft. In some embodiments, the fiber or light guide is configured to couple light into at least one hair shaft through at least one light transmitting surface of the fiber or light guide. Such devices can couple light into one or more hair shafts with or without a coupling enhancing medium, such as any such coupling medium described below, or others. Devices according to the present disclosure are effective, efficient, cost effective, and safe for home use.

In one embodiment, a device configured to cut hair using laser light includes a handle portion and a shaving portion. The handle portion includes a battery and a laser light source. The laser light source is coupled to and configured to receive power from the battery. The laser light source is also configured to generate laser light having a wavelength selected to target a predetermined chromophore to effectively cut a hair shaft. The shaving portion includes a support and a single fiber optic supported by the support. The fiber optic has a proximal end, a distal end, an outer wall, and a cutting region positioned towards the distal end and extending along a portion of the side wall. The fiber optic is positioned to receive the laser light from the laser light source at the proximal end, conduct the laser light from the proximal end toward the distal end, and emit the light out of the cutting region and toward hair when the cutting region is brought in contact with the hair.

The fiber optic may be further configured to prevent light from being emitted from the cutting region when the cutting region is not in contact with the hair. The support may be T-shaped. The support may include a channel configured to receive the fiber optic, and the fiber optic may be positioned within the channel. In some embodiments, the wavelength is within one or more ranges selected from a group consisting of: 380 nm to 480 nm, 380 nm to 500 nm, 400 nm to 500 nm, 2500 nm to 3500 nm, 2950 nm to 3050 nm, and 2700 nm to 3500 nm.

In some embodiments, the shaving portion is removably coupled to the handle portion, the fiber optic is removably coupled to the support, or both. The predetermined chromophore may be selected from the group consisting of: sebum, a fatty acid, phytoshingosine, ceramide, cholesterol, cholesterol sulfate, and cholesterol oleate. In some embodiments, the device also includes an optic configured to direct the laser light from the laser light source to the proximal end of the fiber optic.

In some embodiments, the fiber optic has a diameter in the range of about 4 microns to about 1000 microns. The device may also include a reflector positioned at the distal end of the fiber optic and configured to reflect light towards the fiber optic proximal end. The device may also include a vacuum source coupled to the support and configured to provide aspiration near the cutting region.

In some embodiments, the fiber optic includes a core and a cladding that surrounds the core along the fiber optic length, except at the cutting region. The cutting region may have a radius of curvature that is different than radius of curvature of the fiber optic near its proximal end. In some embodiments, a cross-sectional shape of the fiber optic at the cutting region is wedge-shaped. In some embodiments, the fiber optic tapers in diameter along the cutting region.

In yet another embodiment, a method of shaving hair with laser light includes providing a device configured to cut hair and directing laser light from the device's light source, through its cutting region, and towards a shaft of the hair to cut the hair. The device includes a handle portion and a shaving portion. The handle portion includes a battery and a laser light source. The laser light source is coupled to and configured to receive power from the battery. The laser light source is also configured to generate laser light having a wavelength selected to target a predetermined chromophore to effectively cut a hair shaft.

The shaving portion includes a support and a single fiber optic supported by the support. The fiber optic has a proximal end, a distal end, an outer wall, and a cutting region positioned towards the distal end and extending along a portion of the side wall. The fiber optic is positioned to receive the laser light from the laser light source at the proximal end, conduct the laser light from the proximal end toward the distal end, and emit the light out of the cutting region and towards the hair when the cutting region is brought in contact with the hair.

The method may also include preventing light from being emitted from the cutting region when the cutting region is not in contact with the hair. The method may also include removably coupling: (1) the shaving portion to the handle portion, (2) the fiber optic to the support, or (3) both. The wavelength may be within one or more ranges selected from a group consisting of: 380 nm to 480 nm, 380 nm to 500 nm, 400 nm to 500 nm, 2500 nm to 3500 nm, 2950 nm to 3050 nm, and 2700 nm to 3500 nm.

For purposes of summarizing the disclosure and the advantages achieved over the prior art, certain objects and advantages are described herein. Of course, it is to be understood that not necessarily all such objects or advantages need to be achieved in accordance with any particular embodiment. Thus, for example, those skilled in the art will recognize that the disclosure may be embodied or carried out in a manner that achieves or optimizes one advantage or group of advantages as taught or suggested herein without necessarily achieving other objects or advantages as may be taught or suggested herein. All of these embodiments are intended to be within the scope of the disclosure herein. These and other embodiments will become readily apparent to those skilled in the art from the following detailed description having reference to the attached figures, the disclosure not being limited to any particular disclosed embodiment(s).

BRIEF DESCRIPTION OF THE DRAWINGS

These and other features, aspects and advantages of the present disclosure will be described with reference to the following drawings, which are illustrative but should not be limiting of the present disclosure.

DETAILED DESCRIPTION

Figure 1:
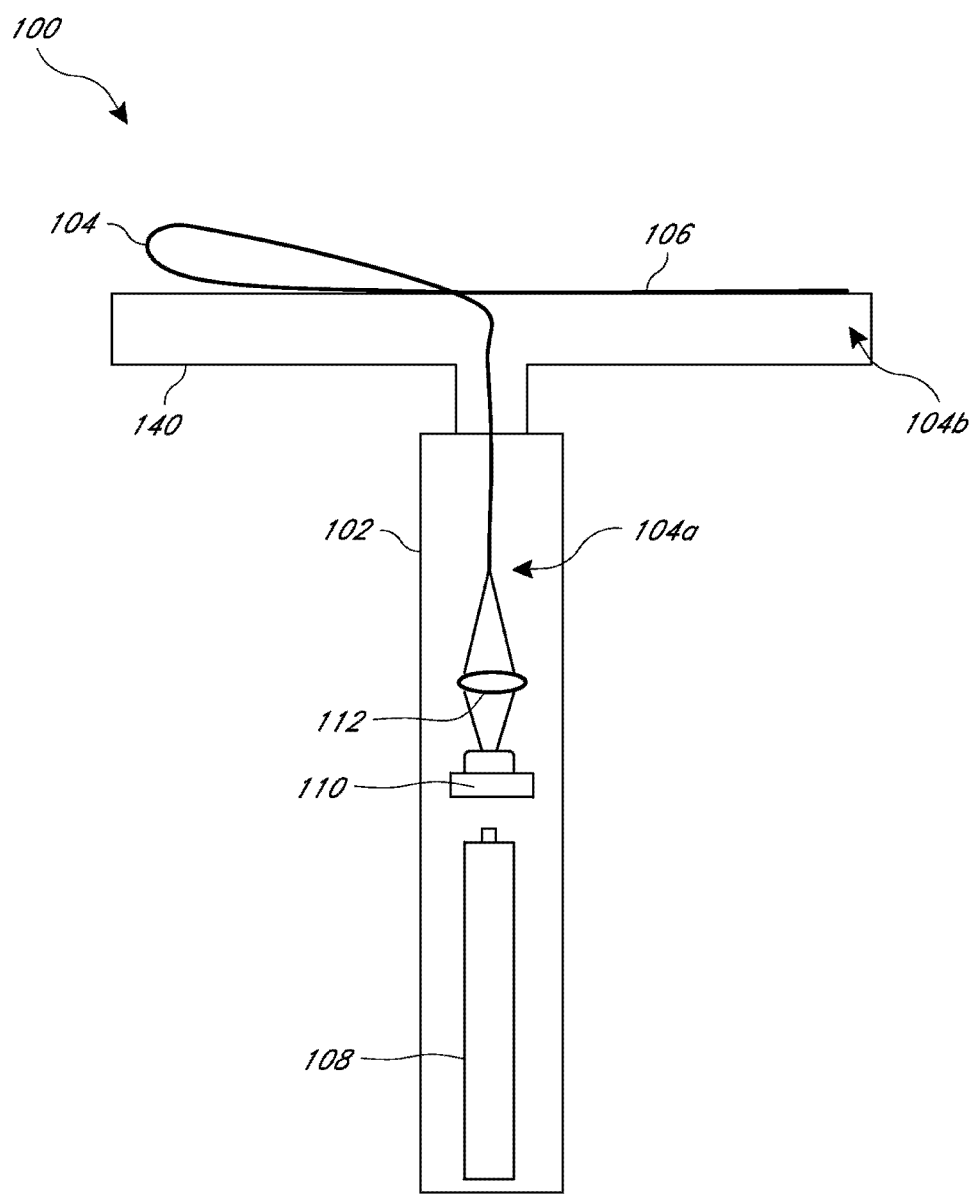
FIG. 1 illustrates an example embodiment of a laser shaving device.

Although certain embodiments and examples are described below, those of skill in the art will appreciate that the disclosure extends beyond the specifically disclosed embodiments and/or uses and obvious modifications and equivalents thereof. Thus, it is intended that the scope of the disclosure herein should not be limited by any particular embodiments described below.

Hair shafts can be severed with high intensity light via absorption heating and burning and/or melting of the shaft. Some optical shaving devices based on this mechanism have been envisioned as an alternative to shaving with razors or laser hair removal. Some such devices include a plurality of optical fibers and are used to cut hair by coupling light into one end of the optical fibers and emitting the light out of the opposite end of the optical fibers and in a direction parallel to their longitudinal axes. One problem with using a plurality of optical fibers in this way is the increased loss of light into the cross-sectional area of the claddings of the multiple fibers. Light energy is lost in the cladding of a fiber as light travels through it, and therefore, more fiber optics results in more light energy loss. In addition, when coupling light from a single light source into a cross-sectional surface (e.g., the proximal end) of a plurality of fibers (e.g., a fiber-optic bundle), an additional problem is fraction losses into the spaces between the fibers, e.g. in the case of round fibers that are bundled together.

Devices and methods according to the present disclosure advantageously overcome these problems and disadvantages associated with cladding cross-sectional losses and/or fraction losses, resulting in a more efficient device. The techniques described herein advantageously allow the devices to be smaller, lighter, and/or less costly to manufacture. In addition, in some embodiments, a single light source is coupled into a single fiber-optic conduit. The single fiber-optic conduit is configured to emit light out of a predetermined area along the side of the fiber's outer wall, as discussed in greater detail below. The side of the fiber's outer wall may be conditioned or configured in a manner that light can only escape out of the side of the fiber's outer wall surface when the outer wall surface is brought into contact with hair. In such cases, intense, energy-focused light is emitted only at such contact locations. This side-firing, focusing effect advantageously results in being able to effectively cut hair (and more generally, to remove matter) using less energy. Therefore, in some embodiments, an efficient shaving device may include a battery powered, hand-held device. In addition, because light is only emitted out of the side of the fiber when in contact with hair (or other targeted matter), the device is safer than devices that continuously emit light out of their distal ends when activated. In addition, the light exiting a side-firing fiber-optic shaving device exits the fiber-optic at a larger divergence angle than an end-firing fiber-optic. Therefore, because of such larger divergence angle, the side-firing fiber-optic shaving device is safer than end-firing devices, as the light from a side-firing device will diverge quicker and become weaker in intensity and fluence (power and energy per area) over distance.

Additionally, to damage and/or cut one or more hair shafts with light, at least some of the light energy is absorbed by the hair shaft and converted into heat or induce a bond breaking mechanism. There are three chromophores in hair that substantially absorb light—melanin, keratin, and water. Keratin and water have absorption peaks at around 3000 nm. Melanin has an absorption peak around 300 nm, but remains relatively flat, decreasing almost linearly (on a logarithmic scale) to about 3000 nm. Darker hair, for example, black and brown hair, contains melanin and can be damaged or cut by sufficient amounts of ultraviolet (UV), visible (VIS), near infrared (NIR), and many infrared (IR) wavelengths. Previous conceptual models, devices, and methods have typically used laser diodes emitting light having a wavelength of about 810 nm to cut or damage the hair. Light having a wavelength about 600 nm is advantageously not absorbed by blood or not absorbed by blood to a large extent, which helps reduce the risk of adverse effects to the patient, as light having a wavelength above about 600 nm is not absorbed by hemoglobin. Some previous devices and methods have attempted to use flash lamps as a light source; however, these have often been impractical for coupling the light into a delivery system.

However, lighter hair, for example, white and blonde hair, has little or no melanin; therefore, previous devices and techniques attempted to cut light hair by targeting water or keratin. Hair normally contains about 12% water. In some cases, when there is no melanin or an insufficient amount of melanin, NIR and/or IR light can be used and absorbed by water to attempt to cut or damage hair. However, when targeting water, if the fluence of the light is not initially sufficient, the water evaporates from the hair shaft and therefore cannot be used in a second attempt to cut or damage the hair shaft. Surprisingly, white light with or without UV light can damage or cut light, for example, white or blonde, hair.

In some embodiments, devices and methods of the present disclosure use one or more of purple (about 400 nm or in the range of about 380 nm to about 480 nm), blue, and/or blue-green light having wavelengths in the range of about 380 nm to about 500 nm or about 400 nm to about 500 nm to damage or cut hair. In some embodiments, light having a wavelength of about 3000 nm is used to damage or cut hair. Surprisingly, light in these ranges is capable of damaging or cutting light hair, for example, even white and blonde hair.

These wavelengths can be selected to target previously unknown chromophores, for example, sebum from the hair follicle. In some embodiments, the wavelengths are selected to target one or more fatty acid(s), phytoshingosine, ceramide, cholesterol, cholesterol sulfate, and/or cholesterol oleate. In some embodiments, the light is selected to target a fatty layer of the hair, on an outer surface of the hair, in the hair, and/or between keratin flakes of the hair. In some embodiments, a user can apply an extrogen chromophore to the hair, the shaving device, or both prior to shaving with any of the devices or according to any of the methods described herein. The extrogen chromophore can be selected to target any desired wavelength(s). These chromophores can advantageously exhibit greater absorption at these wavelengths that previously known chromophores. Additionally, hair typically contains air between layers of keratin. The air pockets can scatter light directed at the hair and increasingly scatter the light as wavelength decreases. Increased scattering lengthens the path of the light in the hair shaft, which increases the probability of the light being absorbed by the hair shaft. The shorter wavelengths in the blue and blue-green range can therefore also cause more scattering, which increases the path length and probability of absorption.

In some embodiments, a shaving device according to the present disclosure can include a single side firing waveguide, such as a laser fiber optic, housed in or supported by a mechanical support. In other embodiments, the shaving device includes more than one fiber. Additionally, in some embodiments, light can be emitted from an end of the waveguide or fiber instead of or in addition to a side.

An example embodiment of a laser shaver 100 is shown in FIG. 1. The shaver 100 includes a handle 102 and a support 140 that supports an optical waveguide, for example, an optical fiber 104, coupled to and extending from the handle 102. The waveguide can be a fiber, a hollow light guide, a liquid light guide, or any other light guide. The handle 102 generally includes a power source 108, at least one light source 110, for example, a diode laser along with any laser driver boards needed, and one or more optics 112. In some embodiments, the light source can be or include a Xenon flash lamp. The light source can be configured to emit various wavelengths of light, for example, between about 2500 nm to about 3500 nm, for example, about 3000 nm, or between about 400 nm to about 500 nm. In some embodiments, the light source can be configured to emit UVA light, UVB light, light that is at least about 20% UVA, light that is at least about 20% in the 400 nm to 500 nm range, light that is at least about 20% in the 2700 nm-3500 nm range, light that is at least about 20% in the 3000 nm range, light that includes UVA light, light that includes light in the range of 380 nm to 480 nm range, light that includes light in the 400 nm to 500 nm range, light that includes light in the 2700 nm to 3500 nm range, light that is substantially in the 400 nm to 500 nm range, light that is substantially in the 2700 nm to 3500 nm range, and/or light that is substantially about 3000 nm or about 3000 nm±500 nm in wavelength. In some embodiments, light sources of different wavelengths can be used with a single fiber 104. In some embodiments, light sources of different wavelengths can be coupled into multiple fibers or other light guides.

The power source 108 is electrically coupled to the light source 110 to power the light source 110. In use, the light source 110 emits light, which is directed to the one or more optics 112. The one or more optics 112 are configured to couple the light from the light source 110 into the proximal end 104a of the fiber 104. The one or more optics 112 can be a lens or lens system or one or more reflectors. In some embodiments, a separate optic is not necessary, and light can be coupled into the waveguide by proximity or direct or indirect contact. In any embodiment according to the present disclosure, the light can be laser light, coherent light, and/or at least one part of non-collimated light. Part or all of the shaver 100 can be waterproof or water resistant. In some embodiments, the light source 110 can be located outside the handle 102, for example in a base unit. The base unit can be electrically and/or optically connected to the handle 102 by an electrical conductor or a light conductor. For example, a fiber or umbilicus can transfer the light from the base unit to the handle 102.

Figure 4:
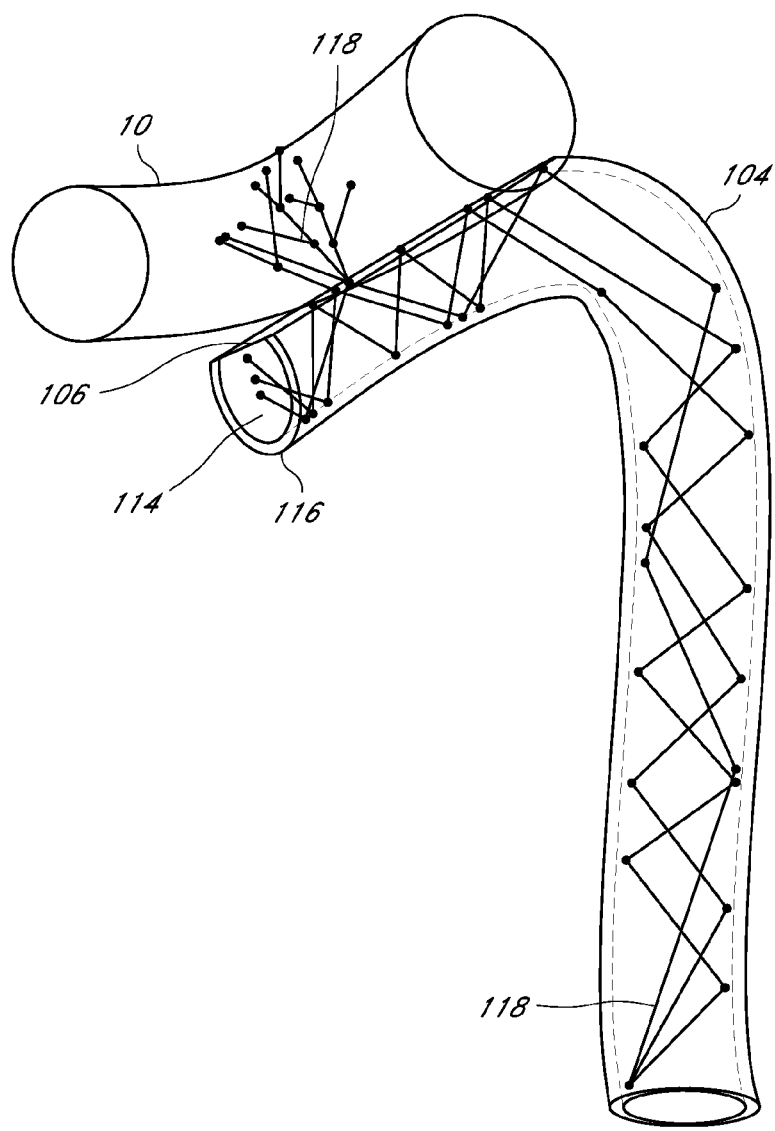
FIG. 4 illustrates a fiber portion of a laser shaver coupling light into a hair shaft.

FIG. 4 illustrates a partial view of the fiber 104. The fiber 104 can have various cross-sectional shapes, for example, round as shown in the illustrated embodiment. As shown, the fiber 104 includes a core 114 and an outer cladding 116 surrounding the core 114. In some embodiments, the fiber core 114 has a diameter in the range of about 4 microns to about 1000 microns. In some embodiments, the fiber core 114 has a diameter between 0.5 mm and 2 mm. In use, light rays 118 propagate along the fiber 104 from the proximal end 104a toward the distal end 104b. The light rays 118 are confined within the core 114 due to the core's higher index of refraction compared to the lower index of refraction of the cladding 116. The fiber 104 includes an aperture or a cutting or light-emitting surface 106 at or near the distal end 104b of the fiber 104. The cutting surface 106 can be shaped to a line having a length of between about 2 mm and about 200 mm. In some embodiments, the cutting surface 106 includes a plurality of optical waveguides or fibers. For example, a single fiber 104 coupled to the handle 102 can couple to a plurality of fibers. In other embodiments, a plurality of fibers or other waveguides can extend from the handle 102. In some embodiments, the cutting surface 106 is positioned along the length of the fiber optic 104, and spaced from the fiber optic's distal end 104b. For example, the entire cutting surface 106 can be spaced a distance from the fiber optic's distal end 104b. The fiber optic 104 may be configured such that the cutting surface 106 does not extend to the fiber's distal end 104b.

Figure 5:
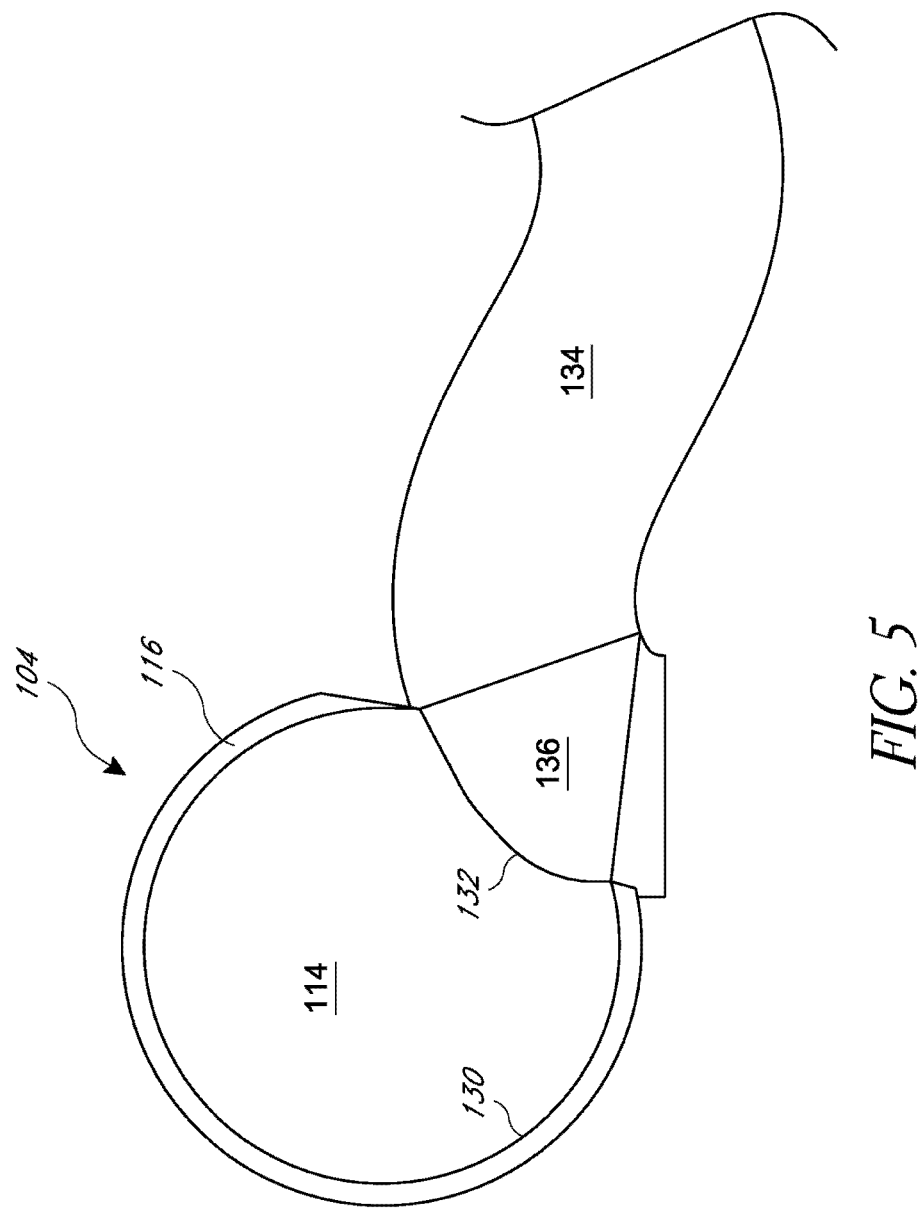
FIG. 5 illustrates a cross-sectional view of another embodiment of a fiber at its cutting region.

FIG. 5 illustrates a cross-sectional view of another embodiment of a fiber 104 at its cutting region. The fiber 104 includes a core 114 and an outer cladding 116 that partially surrounds the core 114. The outer surface 130 of the core 114 includes a contoured portion 132. In the illustrated embodiment, the contoured portion 132 is concave, although in other embodiments, the contoured portion 132 can be convex, planar, pointed, wedge-shaped, etc. The fiber 104 and the cutting region can be formed by drawing, extruding, casting, or equivalent technique. The curvature of the contoured portion 132 can provide a lensing effect to assist in directing light out of the side of the fiber 104 and into the hair shaft 134 by forming an optical focusing region 136 within the hair shaft 134. The contoured portion 132 may be shaped to conform to the hair's outside radius and focus energy inside the hair shaft 134 while bending the hair shaft 134. In some embodiments, the contoured portion 132 is covered at least partially with a coating. For example, a portion of the cladding 116 may be removed from at least a portion of the fiber 104 to expose a portion of the core 114, e.g., on a side of the fiber along its length, and the exposed portion may subsequently be covered by a coating. The coating may be referred to as a "re-cladding." The coating may include any of the coating described above, including but not limited to a clear resin, an organic grease, silicone, petroleum gel, clear PTFE, clear ePTFE, clear rubber, clear RTV, etc. In some embodiments, the coating may be reflective, transmitting, non-reflective, lubricous, and/or configured to grab onto hair.

In some embodiments, the fiber 104 can include a mirror or fiber re-circulator (not shown) at or near a distal end 104b to reflect the light traveling within the fiber 104 to increase light output and efficiency. The mirror can return and help direct at least part of any non-consumed light to the cutting surface 106. In some embodiments, one or more optical reflective coatings are applied to at least part of the fiber 104 to help recycle radiation within the fiber 104 and improve efficiency.

In some embodiments, the shaver 100 also includes a vacuum (not shown), with an optional filter, positioned near or alongside the fiber 104. The vacuum can be configured to remove smoke that may result from burning the hair.

Figure 2:
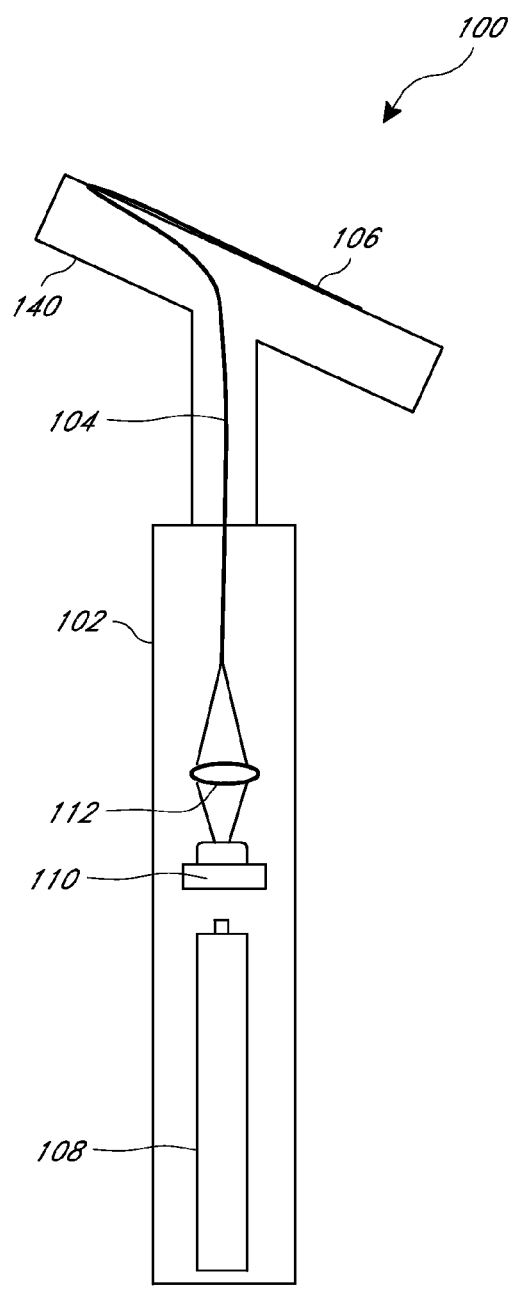
FIG. 2 illustrates another example embodiment of a laser shaving device.
Figure 3:
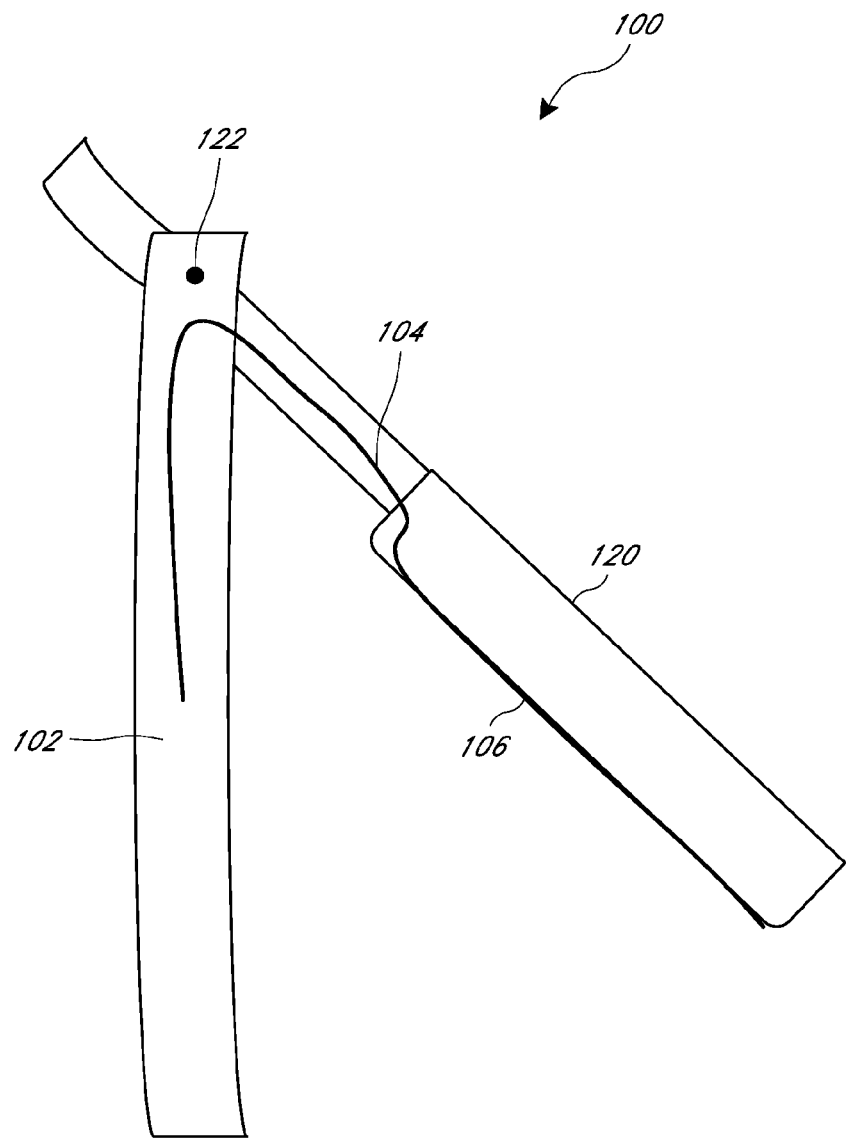
FIG. 3 illustrates another example embodiment of a laser shaving device resembling a straight razor.

The shaver 100 can have various configurations, for example as shown in FIGS. 1-3. The embodiments of FIGS. 1 and 2 have substantially the same handle 102 configuration. However, the fibers 104 and/or supports 140 of the embodiments of FIGS. 1 and 2 have different shapes or configurations. The fiber 104 and/or support 140 can have various shapes and configurations to improve ease of use of the shaver 100. For example, the fiber 104 and/or support 140 can be substantially linear, curved, or include both linear and curved segments. The fiber 104 and/or support 140 can be L shaped, S shaped, T-shaped, or any other suitable shape. In some embodiments, the fiber 104 is held or at least partially contained by a mechanical support 140. Such a mechanical support 140 provides greater strength and structure to the shaver 100 as a single fiber 104 alone could be too flexible to maintain a desired shape and could be more vulnerable to damage. In some embodiments, the shaver 100 can be configured to resemble a traditional bladed razor. In the embodiment of FIG. 3, the shaver 100 is similar to a straight razor. In the illustrated embodiment, the shaver 100 includes a support segment 120 that resembles the blade of a straight razor. The support segment 120 is coupled to the handle 102 via a hinge or pivot 122. In some embodiments, the support segment 120 is pivotally coupled to the handle 102 so that the shaver 100 is foldable. The cutting surface 106 of the fiber 104 can be positioned along an edge of the support segment 120 so that the user can use the shaver 100 in a similar manner as he or she would use a straight razor. In other embodiments, the shaver 100 can resemble a safety razor, and the cutting surface 106 can be positioned where a blade would be in a traditional safety razor.

In some embodiments, the shaver 100 is disposable. In other embodiments, the handle 102 is reusable, and the fiber 104 portion including the mechanical support 140 are disposable, similar to a safety razor having disposable cartridges. The fiber 104 portion can be removably coupled to the handle 102 and can be replaced after a number of uses. The proximal end 104a of the fiber 104 can include a connector configured to couple to a connector on the handle 102. One or both of the connectors can be waterproof or water resistant. In some embodiments, an intermediate waveguide can couple a disposable fiber 104 portion to the handle 102.

In some embodiments, the cutting surface 106 includes a portion of the fiber 104 where the cladding 116 has been removed, for example as shown in FIG. 4. The cladding 116 can be removed via various methods, for example, chemical and/or mechanical methods. Because air has a lower index of refraction than the core 114, the light rays 118 are still confined within the fiber 104. The cutting surface 106 of the shaver 100 must therefore be in contact with hair 10, which has a higher index of refraction than the core 114, for light to be able to couple out of the fiber 104. For example, a fiber 104 having a silica core can have an index of refraction of about 1.47, whereas hair, which is made mostly of keratin with lipids, typically has an index of refraction of about 1.56. In other words, little to no light leaks out of or is emitted from the fiber 104 when the cutting surface 106 is not in contact with the hair or another object having a higher index of refraction than the core. This advantageously confines the laser radiation for safety reasons, for example, for eye safety, and improves the efficiency of the device as the light emitted is used for cutting hair rather than losing light to the room. When the cutting surface 106 is placed into contact with hair 10, the hair shaft begins to draw the radiation from the fiber 104, for example, via evanescent transfer of radiation from the fiber 104 to the hair shaft 10. In some embodiments, the cladding 116 is only removed from a portion of the circumference of the fiber 104 as shown in FIG. 4. This advantageously reduces the risk of a user accidentally contacting another portion of the body with a light emitting portion of the fiber 104. In some embodiments, the shaver 100 can include a sensor configured to detect contact with hair and the shaver 100 can be configured such that the light source 110 is only turned on or active when the cutting surface 106 is determined to be in contact with hair.

In some embodiments, light is coupled out of the fiber 104 at the cutting surface 106 by using a coating or coupling material, instead of or in addition to removal of the cladding 116. In some such embodiments, the cutting surface 106 does not have to be in contact with hair to emit light. For example, the cutting surface 106 can be processed with photolithography or etching to create a surface that allows light to exit the fiber 104. In some embodiments, a scatting material can be coupled, e.g., glued or adhered, to the cutting surface 106. In some embodiments, both the cladding 116 is removed from the cutting surface 106 and the cutting surface 106 is further processed or a scattering material is coupled to the cutting surface 106. In some embodiments, one or more coatings are applied to at least part of the fiber 104 to enhance energy transfer to the hair shaft. Such coating may optionally be applied to the hair as well (or instead of applying such materials to the fiber 104). Any of a variety of coating or coupling materials may be used, including but not limited to, any of the chromophores discussed herein, petroleum gel, a resin, silicone, room-temperature vulcanization silicone (RTV), polytetrafluoroethylene (PTFE), expanded polytetrafluoroethylene (ePTFE), etc. In some embodiments, the fiber 104 or cutting surface 106 is shaped to optimize radiation transfer to the hair. For example, a distal portion of the fiber 104 can be tapered to change the angles of light being propagated within the fiber until at least some of the light couples out of the fiber 104.

In some embodiments, the shaver 100 includes at least one light front cross-section shaping optic that at least partially arranges coherent light along a line of between about 2 mm and about 200 mm. In some such embodiments, the light passes directly from the light shaping optic to the hair. In other embodiments, the light passes through at least one more optic to be directed to the hair. In some embodiments, the light shaping optic is a waveguide or fiber that at least partially changes the shape of light emitted to a line having a length of between about 2 mm and about 200 mm. In some embodiments, light from the light source is coupled into at least one blade shaped optic that guides at least part of the light to the hair. The blade shaped optic can be a light guide and/or a light transmitter. The blade shaped optic can be detachable, consumable, and/or exchangeable.

For eye safety and/or skin comfort and/or safety, the light is preferably not emitted directly toward the hair, face, or other body parts. In some embodiments, the shaving device is configured to direct the light emitted in a direction parallel or substantially parallel to the skin surface or at an angle selected such that the light does not substantially enter the skin and/or eyes. For example, the shaver 100 and cutting surface 106 can be configured such that light incident on the hair is aimed toward the hair at an angle in the range of about ±45°, for example, in the range of about ±5°, ±10°, or ±25°, to the surface of the skin. In some embodiments, the shaver 100 includes at least one sensor configured to detect a broken fiber. For example, a sensor can be positioned at or near the distal end 104b of the fiber 104 and can detect the amount of light incident on the sensor. If little or no light is reaching the sensor at the distal end 104b, the fiber 104 may be broken and allowing radiation to leak out, which can create a safety hazard. Therefore, if the sensor detects little or no light reaching the distal end 104b, the shaver 100 can turn off the light or power source.

When cutting white (or light) hair with blue light, e.g., at about 403 nm, approximately twice the fluence (or energy level) is needed compared to cutting brown hair (for example, by targeting melanin). Increasing the power can therefore improve the efficacy of the devices and methods described herein in some cases; however, increasing the power can also increase the risk of adverse effects in some cases. In some embodiments, a shaving device as described herein includes one ore more sensors configured to detect or gather data indicative of the chromophore(s) present in the target hair. For example, upon contact with the hair, the device can emit light into the hair, and a sensor can detect the light reflected to allow the device to determine the wavelengths of light absorbed. In some embodiments, the sensor could be located in the handle of the device. In some embodiments, the sensor can be a MEMS device that functions as a spectrometer and is located on the portion of the device configured to emit light to and/or contact the hair. If the sensor detects and/or the device determines based on sensor data that the hair contains a sufficient amount of melanin, the device can reduce the energy level or power and/or adjust the wavelength of light emitted to target a predetermined chromophore (e.g., melanin). If the sensor detects and/or the device determines based on sensor data that the hair lacks sufficient melanin but contains sufficient sebum, the device can increase the energy level or power and/or adjust the wavelength emitted to target the sebum.

More than one device as described herein can be used synchronously or in sequence to cut or damage hair.

Although the devices and methods herein have been described with respect to cutting or damaging hair, these devices and methods can be used for other applications, for example, surgery. The device or cutting surface 106 can be shaped similar to a knife, surgical scalpel, or other cutting tool. In some embodiments, when using the device to cut tissue, the device can also act as a coagulating and bleeding stopping means by means of the heat created by light absorbed into the tissue. The light can be modulated and tuned to cut tissue or coagulate.

It should be emphasized that many variations and modifications may be made to the embodiments described herein, the elements of which are to be understood as being among other acceptable examples. All such modifications and variations are intended to be included herein within the scope of this disclosure and protected by the following claims. Further, nothing in the foregoing disclosure is intended to imply that any particular component, characteristic or process step is necessary or essential.

What is claimed is:

1. A device configured to cut hair using laser light, the device comprising:
    a shaving portion configured to be coupled to a handle portion, the shaving portion comprising:
        a support, and
        a fiber optic supported by the support, the fiber optic having a proximal end, a distal end, an outer side wall, and a cutting region positioned towards the distal end and extending along a portion of the outer side wall,
    wherein the shaving portion is configured to provide laser light having a wavelength selected to target a chromophore to cut a hair shaft,
    wherein the fiber optic is positioned to receive the laser light at the proximal end, conduct the laser light from the proximal end toward the distal end, and emit at least a portion of the laser light out of the cutting region and toward hair when the cutting region is brought in contact with the hair.

2. The device of claim 1, wherein the fiber optic is further configured to prevent light from being emitted from the cutting region when the cutting region is not in contact with the hair.

3. The device of claim 1, wherein the support comprises a bend.

4. The device of claim 1, wherein the support comprises a channel configured to receive the fiber optic, and wherein the fiber optic is positioned within the channel.

5. The device of claim 1, wherein the wavelength is within one or more ranges selected from a group consisting of: 380 nm to 480 nm, 380 nm to 500 nm, 400 nm to 500 nm, 2500 nm to 3500 nm, 2950 nm to 3050 nm, and 2700 nm to 3500 nm.

6. The device of claim 1, further comprising the handle portion, and wherein the shaving portion is configured to be removably coupled to the handle portion.

7. The device of claim 1, wherein the fiber optic is removably coupled to the support.

8. The device of claim 1, wherein the chromophore is selected from the group consisting of: sebum, a fatty acid, phytoshingosine, ceramide, cholesterol, cholesterol sulfate, cholesterol oleate, water, keratin, and melanin.

9. The device of claim 1, further comprising an optic, the optic configured to direct the laser light toward the proximal end of the fiber optic.

10. The device of claim 1, wherein the fiber optic has a diameter in the range of about 4 microns to about 1000 microns.

11. The device of claim 1, further comprising a reflector positioned at the distal end of the fiber optic and configured to reflect at least a portion of the laser light towards the fiber optic proximal end.

12. The device of claim 1, further comprising a vacuum source coupled to the support and configured to provide aspiration near the cutting region.

13. The device of claim 1, wherein the fiber optic comprises a core and a cladding that surrounds the core along the fiber optic length, except at the cutting region.

14. The device of claim 1, wherein the fiber optic has a radius of curvature at the cutting region that is different than the radius of curvature of the fiber optic near its proximal end.

15. The device of claim 1, wherein a cross-sectional shape of the fiber optic at the cutting region is wedge-shaped.

16. The device of claim 1, wherein the fiber optic tapers in diameter along the cutting region.

17. The device of claim 1, wherein an index of refraction of the fiber optic is less than an index of refraction of the hair shaft.

18. The device of claim 17, wherein the index of refraction of the fiber optic is greater than an index of refraction of air.

19. A method of shaving hair with laser light, the method comprising:
   providing a device configured to cut hair, the device comprising:
      a shaving portion configured to be coupled to a handle portion, the shaving portion comprising:
         a support, and
         a fiber optic supported by the support, the fiber optic having a proximal end, a distal end, an outer side wall, and a cutting region positioned towards the distal end and extending along a portion of the outer side wall,
         wherein the shaving portion is configured to provide laser light having a wavelength selected to target a chromophore to cut a hair shaft,
         wherein the fiber optic is positioned to receive the laser light at the proximal end, conduct the laser light from the proximal end toward the distal end, and emit at least a portion of the laser light out of the cutting region and towards the hair when the cutting region is brought in contact with the hair; and
   directing the laser light through the cutting region, and towards a shaft of the hair to cut the hair.

20. The method of claim 19, further comprising preventing light from being emitted from the cutting region when the cutting region is not in contact with the hair.

21. The method of claim 19, further comprising removably coupling: (1) the shaving portion to the handle portion, (2) the fiber optic to the support, or (3) both.

22. The method of claim 19, wherein the wavelength is within one or more ranges selected from a group consisting of: 380 nm to 480 nm, 380 nm to 500 nm, 400 nm to 500 nm, 2500 nm to 3500 nm, 2950 nm to 3050 nm, and 2700 nm to 3500 nm.

23. The method of claim 19, wherein an index of refraction of the fiber optic is less than an index of refraction of the hair shaft.

24. The method of claim 23, wherein the index of refraction of the fiber optic is greater than an index of refraction of air.

* * * * *